US006770248B2

(12) United States Patent
Haggett et al.

(10) Patent No.: US 6,770,248 B2
(45) Date of Patent: Aug. 3, 2004

(54) FLOWTHROUGH DEVICE FOR THE ULTRASONIC DESTRUCTION OF MICROORGANISMS IN FLUIDS

(75) Inventors: Randall D. Haggett, Dartmouth (CA); Kenneth J. KarisAllen, Halifax (CA); Guerorgui A. Hranov, Toronto (CA)

(73) Assignee: Her Majesty the Queen in right of Canada, as represented by the Minister of National Defence of Her Majesty's Canadian Government, Ottawa (CA)

(*) Notice: Subject to any disclaimer, the term of this patent is extended or adjusted under 35 U.S.C. 154(b) by 454 days.

(21) Appl. No.: 09/848,418

(22) Filed: May 4, 2001

(65) Prior Publication Data

US 2002/0164274 A1 Nov. 7, 2002

(51) Int. Cl.[7] .......................... B01D 17/00; B08B 3/12; C02F 1/36; B06B 1/00
(52) U.S. Cl. ...................... 422/128; 422/20; 134/184; 210/542; 210/748
(58) Field of Search ................... 422/128, 20; 134/184; 210/542, 748

(56) References Cited

U.S. PATENT DOCUMENTS

| 4,086,057 A | * | 4/1978 | Everett ........................ 422/128 |
| 5,395,592 A | | 3/1995 | Bolleman et al. |
| 6,540,922 B1 | * | 4/2003 | Cordemans et al. ........ 210/695 |

FOREIGN PATENT DOCUMENTS

| CA | 2151874 | 6/1995 |
| DE | 1 944 532 | 9/1969 |
| DE | 44 36 054 A1 | 10/1994 |

OTHER PUBLICATIONS

R. Haggett et al; "Microbiological Contamination : Biocide Treatment in Naval Distillate Fuel"; Int'l Biodeterioration and Biodegradation 29 (1992) pp. 87–99.
G. Scherba et al.; "Quantitative Assessment of the Germicidal Efficacy of Ultrasonic Energy"; Applied and Environmental Microbiology 1991, 2079–2084.
H. Kinsloe et al; "Exposure of Microorganisms to Measured Sound Fields"; J. Bacteriology 68 (1954); 373–380.
A.J. Ciesluk; "Ultrasound for Shipboard Waste Disposal"; U.S. Navy Coastal Systems Station Technical Report NCSC–TR–329–79 (Abstract).
E.C. Hill; "Fuels"; Microbial Problems in Offshore Oil Industry, pp 219–229.
Betts et al.; "Ultrasonic Standing Waves/Inactivation of Food–borne Microorganisms using Power Ultrasound"; Encyclopedia of Food Microbiology, pp. 2202–2208.
Burgos; "Minimal Methods of Processing/Manothermosonication"; Encyclopedia of Food Microbiology; pp. 1462–1469.

* cited by examiner

Primary Examiner—Hoa Van Le
(74) Attorney, Agent, or Firm—Stites & Harbison, PLLC; Ross F. Hunt, Jr.

(57) ABSTRACT

An apparatus for the ultrasonic destruction of microbiological contamination of fluids. The process involves subjecting contaminated fluids to ultrasonic vibration so as to cause cavitation within the fluids. The cavitation results in the destruction of microbial cells and mats of microbial colonies. To create cavitation in the fluids a number of piezoelectric ceramic rings surround a metal tube through which the fluids flows. Those piezoelectric rings are immersed in a transmission medium which is pressurized sufficiently to prevent cavitation occurring in it and causing damage to the piezoelectric rings electrodes. This process is applicable to many liquids such as fuels, lubricating fluids, potable and marine ballast waters, dairy products, pharmaceuticals, liquid food products and beverages.

12 Claims, 5 Drawing Sheets

FLOWTHROUGH DEVICE FOR THE ULTRASONIC DESTRUCTION OF MICROORGANISMS IN FLUIDS

FIELD OF THE INVENTION

The present invention relates to a method and apparatus for the control of microbial contaminants in liquids and, more particularly, to the destruction of such contaminants in shipboard fuels and ballast waters by the use of ultrasonic vibration to cause cavitation within these liquids, that apparatus being designed to prevent cavitation from damaging parts of the apparatus that create the ultrasonic vibrations.

BACKGROUND OF THE INVENTION

Microbiological contamination of hydrocarbon fuels presents a variety of problems to the operators of naval vessels. Some of the organisms responsible for such contamination are fungi, yeast and bacteria.

In naval vessels, it is common for water to be found in on board fuel tanks. This water originates from various sources such as condensation from the fuel, water leakage into the fuel or from water taken on as ballast in the tanks. The presence of water in the fuel tank results in the proliferation of yeasts and fungi at the fuel/water interface where the microbial contaminants extract oxygen from the water and nutrients from the fuel layer. Some forms of these microorganisms produce water as a byproduct, thereby altering the environment of the fuel/water interface and allowing other microbial forms to flourish.

Various problems arise from the microbiological contamination of fuel including:

(a) Mat-like or slimy deposits at the fuel/water interface;
(b) Blockages of valves, pumps, filters and coalescers;
(c) Reduction in interfacial tension resulting in the malfunction of water separating devices;
(d) Accelerated corrosion of steel and aluminum;
(e) Black stains on copper alloys or silver plated components;
(f) Injector fouling; and
(g) Probe fouling and incorrect volume measurement.

Some of these problems have previously been documented (R. D. Haggett and R. M. Morchat, *Intl. Biodeterioration & Biodegradation* 29 (1992) 87–99).

These consequences can be tolerated at minor levels of infection. However, as the microbial population flourishes, serious and costly failures are inevitable. Generally, contamination problems are only investigated when the failure or malfunction of equipment occurs. Fuel tanks, and associated systems, found to contain such contaminants must be drained, cleaned, dried and inspected prior to being reused.

Completely sterile natural environments are rare and without strong chemical additives toxic to microbes, some level of contamination can always be expected. However, if the levels of this contamination can be kept below critical levels, their proliferation can be prevented and the damaging consequences avoided.

The only means of controlling microbiological contamination in ship board fuel systems at present is to prevent water from accumulating in fuel tanks, which is extremely difficult and impractical, or to treat the contaminated fuel with biocidal agents. However, the use of such biocides presents environmental and health and safety concerns. Questions have arisen concerning the effect of biocide containing fuel on personnel working daily with fuel system components as well as personnel working in confined spaces where they may be exposed to vapours containing the biocide. The environmental concern relates to the effect that such biocidal agents may have if introduced into already sensitive marine ecosystems. The selective nature of biocides presents a further problem in their usage. For example, while some biocides are effective against fungi they have little or no effect on bacteria. Further, while some biocides inhibit growth of pure microbial cultures, their effectiveness is drastically reduced when applied to mixtures of fungi, yeasts and bacteria.

The use of ultrasound as a germicidal agent has been investigated previously by G. Scherba et al (*Applied and Environmental Microbiology* 1991, 2079–2084) and H. Kinsloe et al (*J. Bacteriology* 68 (1954) 373–380). The literature on the treatment of microorganisms using ultrasonics is sparse, but all studies that have been carried out agree that it is an effective means of destroying microorganisms. A shipboard application of this technology is waste water treatment. This possibility was studied by the U.S. Navy Coastal Systems Station in 1976 (A. J. Ciesluk, "Acoustic Sterilization For Shipboard Waste Management", U.S. Navy Coastal Systems Station Technical Report, NCSC-TR-329-78). In this study, two commercial ultrasonic cleaners were used at two different power levels. However, it was concluded that the basin volumes of these cleaners were too large to lead to effective cell disruption. That literature does not describe the use of ultrasound to control microbial populations in fuel systems although the possibility has been proposed (E. C. Hill (1986), "Microbial Problems In Offshore Oil Industry" Proceedings of the International Conference, Inst. Petroleum Microbiology Committee, Aberdeen, U.K.).

Because of its inherent safety and relatively low power requirements compared to other physical control measures, ultrasound may represent the ideal solution to microbiological contamination of fuel systems. If the fuel and/or the water in the vicinity of the fuel/water interface is treated on an ongoing basis, the microbial populations can likely be kept below critical levels. This would represent a more environmentally friendly and more effective control measure than the biocides currently in use.

SUMMARY OF THE INVENTION

Accordingly, it is an object of the present invention to overcome the limitations of known fuel decontamination methods and provide a safe and effective process for the control of microbial populations in fuel systems. It is also an object of the present invention to provide a system and a process for the effective treatment of microbiologically contaminated ballast waters prior to disposal thereof.

Specifically, the present invention is directed to an apparatus for neutralizing microbiological contamination of a liquid fuel comprising subjecting the fuel to ultrasonic vibrations in order to cause cavitation within the liquid and, thereby, to destroy the microbial contaminants and which is designed to avoid any cavitation from damaging the parts of the apparatus that create the ultrasonic vibrations.

An apparatus for the ultrasonic treatment of a microbiologically contaminated liquid, according to one embodiment of the invention, comprises:

a module having a treatment container and an ultrasonic generating means for subjecting ultrasonic vibrations on the liquid in the container where contaminated liquid in the container subjected to the ultrasonic vibrations result in cavitation in the liquid and the destruction of microorganisms contained therein, the ultrasonic vibration generating means being located outside of the container and submerged in a transmission fluid pressurized to prevent cavitation occurring at areas surrounding the ultrasonic generating means.

DESCRIPTION OF THE DRAWINGS

These and other features of the invention will become more apparent in the following detailed description in which reference is made to the appended drawings wherein.

DETAILED DESCRIPTION OF THE PREFERRED EMBODIMENTS

A flowthrough ultrasonic system for destruction of microorganisms in fuels and ballast waters was described by Randall Haggett et al in Canadian Patent Application 2,151,874 that was filed on Jun. 15, 1995. A series of potential configurations for the design of Ultrasonic Destruction of Microorganisms (UDM) have been built and evaluated. These configurations included:

(1) a flowthrough bank of ultrasonic horns;
(2) a submerged coil; and
(3) piezoelectric rings.

The ring concept appears to be the most suitable at providing a fairly even distribution of energy in a fluid such as diesel fuel. There were problems, however, associated with this concept. The generation of cavitation to kill microorganisms in the fluid was accompanied by serious erosion problems associated with that cavitation. Initial tests with the piezoelectric ceramic ring concept showed that the erosion would drastically limit the life of the electrodes on the ceramics and then the ceramic rings themselves. In early tests, the electrodes were being eroded in minutes. Various coatings for protection from cavitation erosion were tested on the ceramic rings and evaluated for power transfer characteristic as well as erosion protection. None were found to provide satisfactory protection. A solution to that problem, according to the present invention, was the introduction of a second fluid (a transmission medium) around the ceramic rings and their electrodes. That second fluid was selected to minimize cavitation around the piezoelectric rings while transmitting ultrasonic energy to an inner tube through which the fluid to be decontaminated flowed.

Figure 1:
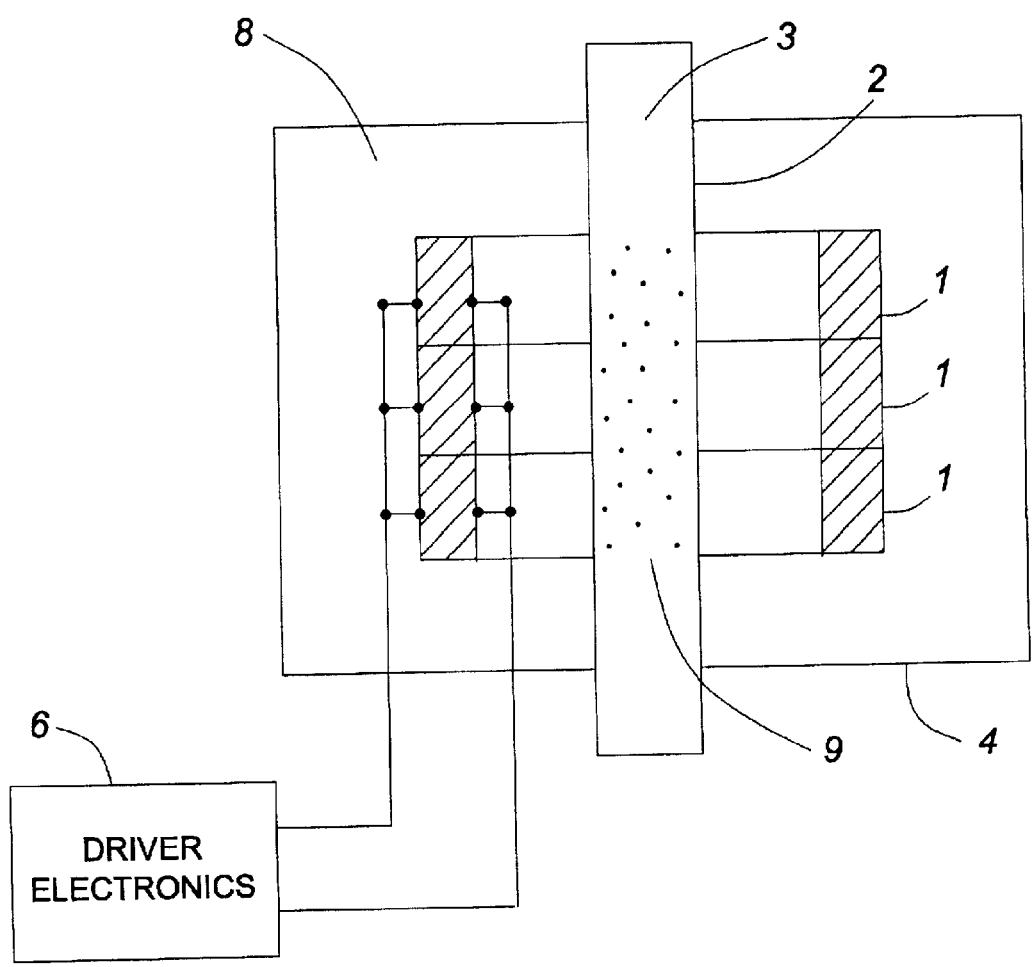
FIG. 1 is a schematic view of an ultrasonic decontamination system according to the present invention.

The basic concept of an ultrasonic decontamination system according to the present invention is illustrated, schematically, in FIG. 1. A number, three being shown in FIG. 1, of piezoelectric ceramic rings (or elements) 1 surround an inner metal tube 2 that forms a treatment container through which a fluid 3 to be decontaminated, such as diesel fuel, flows. The rings 1 are connected to and electrically excited by driver electronics 6 to generate ultrasonic sound of an intensity to create destruction of microorganisms in that diesel fuel. The generated ultrasonic sound is sufficiently intense to induce cavitation in the liquid 3, illustrated by bubbles 9 in FIG. 1, and it is this cavitation 9 that is responsible for microorganism destruction in the liquid 3. The piezoelectric rings 1 are immersed in a transmission medium 8 in container 4, the transmission medium 8 in container 4 being pressurized to a pressure sufficient to prevent cavitation occurring in that transmission medium. If cavitation were allowed to occur in the medium in contact with the piezoelectric rings, destruction of the thin metal coated electrodes on the rings would rapidly occur because of surface erosion action caused by cavitation. Pressurization of the medium prevents cavitation occurring and damaging the piezoelectric rings electrodes.

Figure 2:
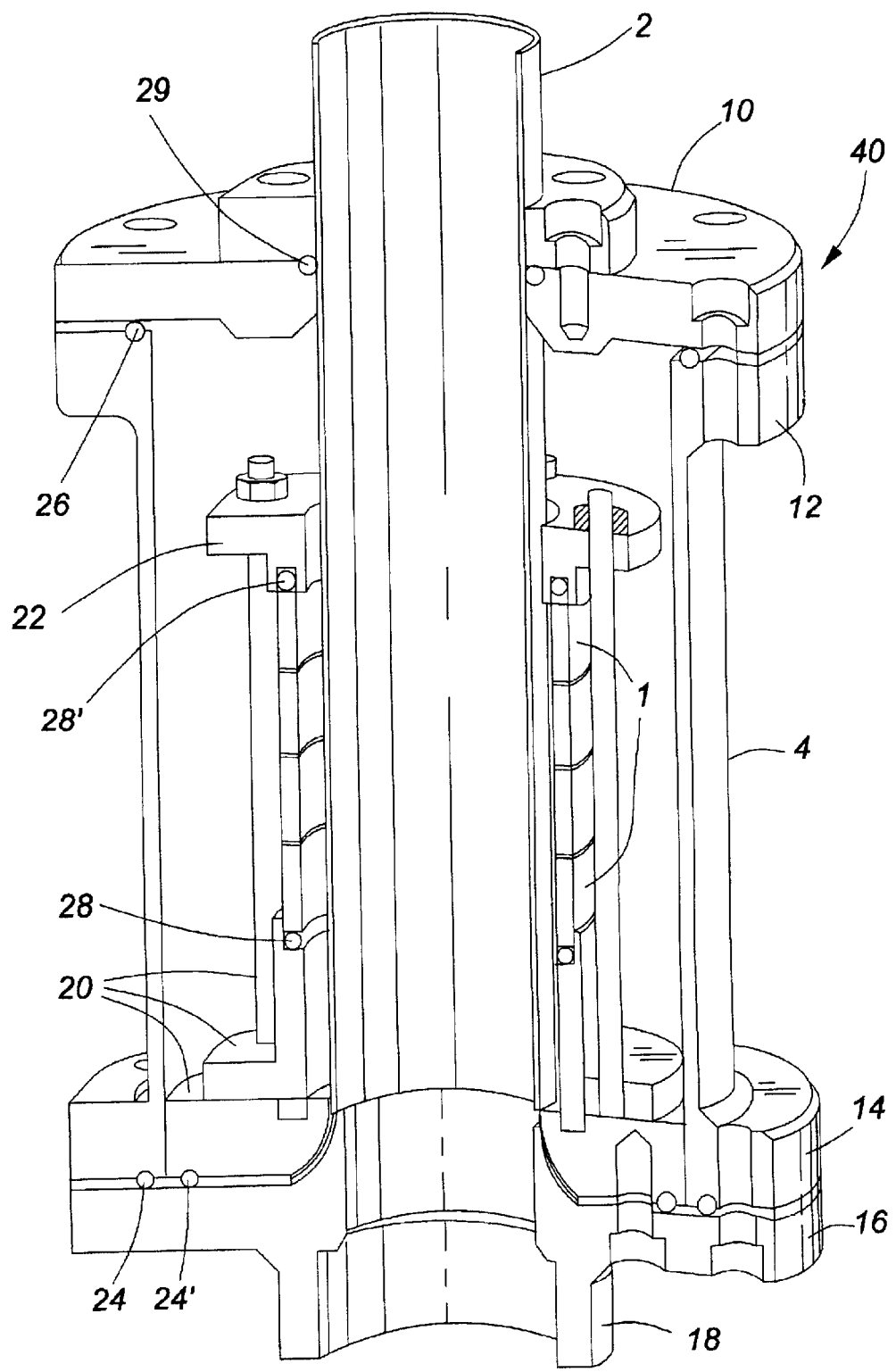
FIG. 2 is a cross-sectional view of the ultrasonic decontamination system according to the present invention.

A prototype mechanical module (or cavitator) 40 for an ultrasonic decontamination system according to the present invention was built and consisted of 4 piezoelectric rings stacked axially around a 1.5 inch outside diameter (OD) stainless steel tube 2 as illustrated in the cross-sectional view in FIG. 2. The housing design is such that the transmission fluid surrounding the piezoelectric rings 1 can be pressurized and the liquid to be decontaminated can be pumped continuously through the tube.

The prototype module, according to one embodiment of the invention and illustrated in FIG. 2, has an outer housing 4 with a bottom flange 14 and top flange 12 with a bottom 16 being attached to flange 14 and a cover 10 attached to flange 12 to form a chamber to hold a transmission medium such as oil. These components were formed of aluminium in this prototype but might be formed of stainless steel in other systems so as to avoid possible corrosion problems.

The bottom 16 has a central opening formed by protrusion 18 with that central opening being connected to a stainless steel inner tube 2 that extends through the chamber and out through a central opening in the cover 10. The inner tube 2 is swaged onto a flared section on an extension of protrusion 18 that protrudes into the chamber and an O-ring 24' between a support structure 20 attached to flange 16 and flange 16 effects sealing at that end. The tube is sealed at the other end by an O-ring 29 between the cover 10 and tube 2. This allows the tube to expand and contract freely (except for friction of the O-ring) at that end so as to accommodate manufacturing tolerances and thermal expansion/contraction.

A support structure 20 is connected to bottom 16 and supports four piezoelectric ceramic rings 1 around the inner tube 2. The rings each have a 2 inch OD, a 1.75 inch ID, a 0.55 inch length and are stacked one above the other. The rings are mounted between nylon flanges with silicone rubber O-ring separators 28, 28'. The separators avoid overconstraining the rings and prevent any buildup of axial stress due to differential thermal expansion between the components as temperature changes occur. The piezoelectric ring assembly is fixed in the chamber and the electric connections to it are brought out to a connector (not shown) on the cover 10. An O-ring 24' is located between the bottom of support 20 and bottom 16 and another 24 is located between bottom 16 and flange 14 to seal the chamber at that end. An O-ring 26 between the top flange 12 and cover 10 seals the chamber at the top end.

To allow filling the chamber formed by components 4, 10 and 16 with a transmission medium without trapping air in that chamber, a fill hole (not shown) is provided at the bottom and an air release vent (not shown) is provided at the top with a circular groove being machined in top 10 to collect air from all points around the circumference and lead it to the air release vent. That vent is sealed with a screw after the chamber is filled and the air vented. Once the chamber is filled with the transmission medium, it surrounds the piezoelectric rings 1 and transmits ultrasonic energy generated by the rings to the inner tube 2 through which a fluid to be decontaminated flows.

The transmission medium in the chamber must have the following characteristics:
1. be electrically insulating;
2. be compatible with all material that it contacts, such as the aluminium (or stainless steel) housing, the inner tube, the nylon (or other plastic) support used to mount the piezoceramic rings, the ceramic rings and their silver or nickel electrodes;
3. be resistant to cavitation when pressurized to low levels; and
4. have a low loss to acoustic energy.

Possible fluids that could be used as a transmission medium are natural and synthetic lubricating oils, transformer oil, or oils used in some high power sonar transducers. In this prototype system, ordinary SAE 10W30 motor oil was used as a transmission medium.

Once the chamber is filled with the transmission medium, that medium must be pressurized to a controlled level to prevent cavitation in it. In this prototype system, that pressurization was accomplished by using a small hydraulic cylinder 37 (see FIG. 3) connected to the chamber and which is loaded by a manually adjusted screw 38. Another method would be to use an air cylinder rather than a screw to load the hydraulic cylinder. Thermal expansion of the oil as the temperature rises during operation causes the pressure to rise making the screw and hydraulic cylinder difficult to control. To alleviate that problem, a small bellows or expansion bulb could be added to the fill port.

The inner tube 2 through which the liquid to be decontaminated flows is formed of stainless steel in order to ensure maximum compatibility with a ship's diesel fuel. The tube 2 should be as thin as possible to avoid screening the acoustic field from the medium in the pipe but thick enough to avoid collapse under the external pressure caused by the pressurization of the transmission medium in the chamber. The tube 2 used in this prototype system had a 0.012 inch wall thickness and an outside diameter (OD) of 1.5 inch.

Figure 3:
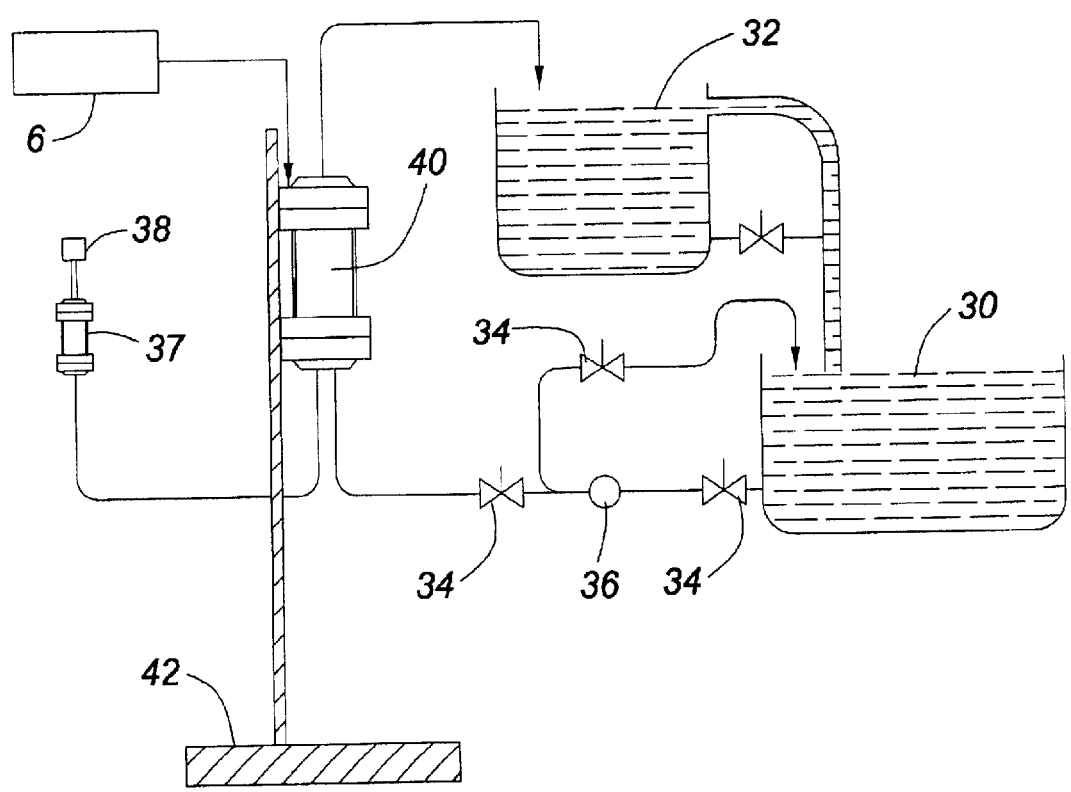
FIG. 3 is a schematic view of a flow-through test system according to one embodiment of the present invention.

The test assembly of the prototype flowthrough system is schematically illustrated in FIG. 3. In that system, a tank 30 contains contaminated water which is pumped by pump 36 through pipes and valve assembly 34 to a decontamination module 40 mounted on a stand 42. A power supply 6 is connected to the top of module 40 and treated water exits from the top of module 40 and is then piped to tank 32.

The flow rate through the module is dictated by the duration which the liquid in tube 2, such as diesel fuel, must be exposed to the ultrasonic field in order to obtain an adequate microorganism kill rate. The flow rate is also dependent on the type of application. It need not kill all microorganism in a single pass, for instance, if the system is run continuously with fuel circulating from a tank to the module, through the system, then back to the tank with the goal of keeping microorganism growth down. If the goal is to attempt to sterilize fuel that has been brought on board from a contaminated source, or which is being off-loaded after contamination has been allowed to build up, then a high kill rate would be required. This would, therefore, require a lower flow rate through the module resulting in a longer residence time.

The prototype module was designed with the criterion that the fuel should be exposed to the most intense sound field (assumed to be directly adjacent to the piezoelectric rings) for 4 seconds. That time was based on experience with an experimental unit where, at least for some organisms, the required kill rate was achieved in 4 seconds. With the dimensions used in this module, a flow rate through the module of 15 Imperial gallons per hour (GPH) would be sufficient. If shorter durations are found to be acceptable, greater flow rates can be used. The pressure drop through the tube is very small at these flow rates.

Figure 4:
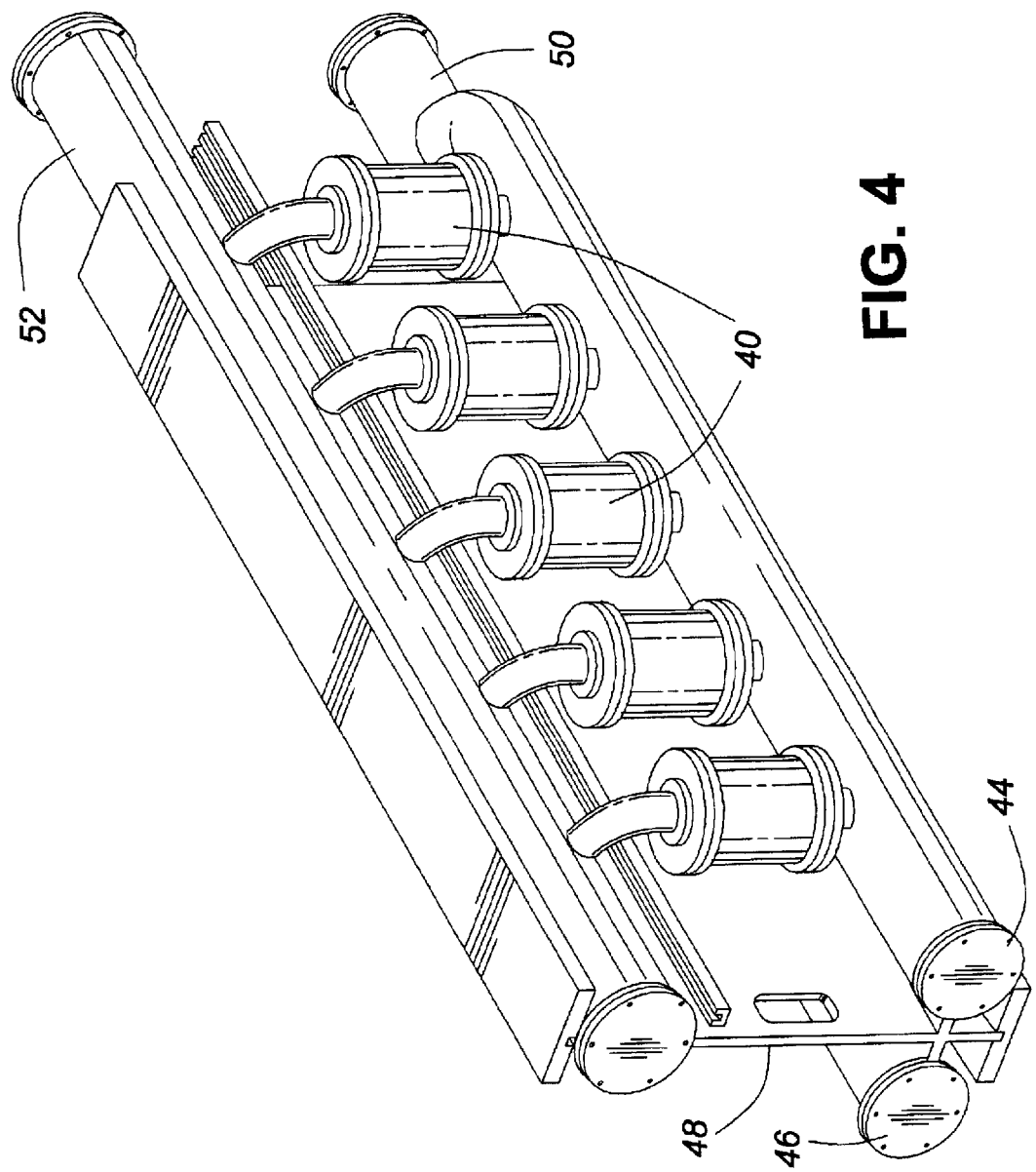
FIG. 4 is a perspective view of a bank of ultrasonic decontamination modules connected in parallel according to a further embodiment of the present invention.
Figure 5:
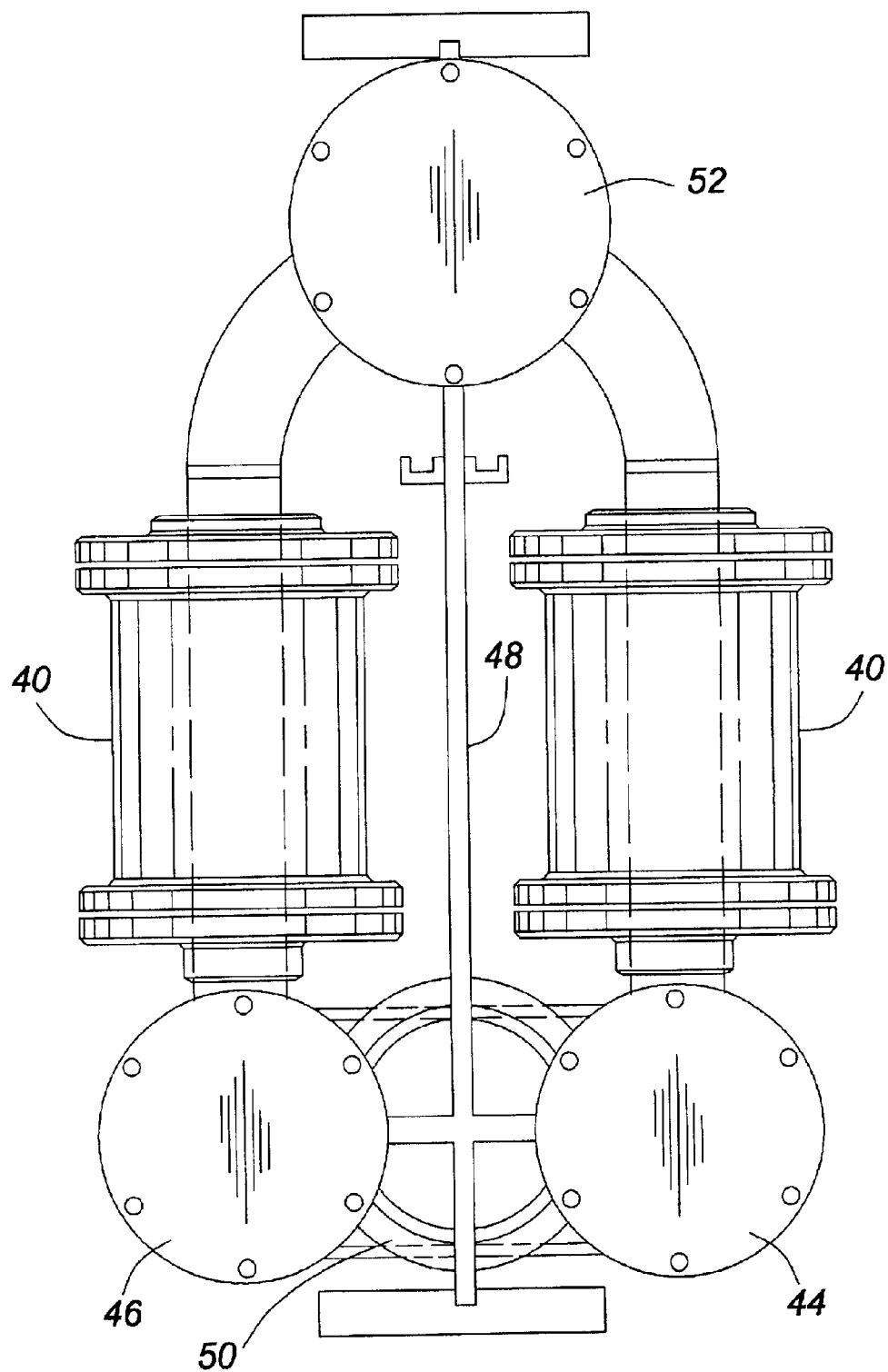
FIG. 5 is a front view of the embodiment shown in FIG. 4.

Decontamination modules, similar to those previously described can be arranged into banks where a number of modules 40 are connected in parallel between an input manifold 50 and an output manifold 52 assembled on support 48 as shown in FIG. 4. The input manifold 50 is divided into two input manifolds 44 and 46 located on each side of a central support 48 (see FIG. 5) with 5 modules being connected between each inlet manifold 50 and the output 52 on each side of support 48. If each module has a flow rate of 15 GPH, then the total flow through the bank illustrated in FIGS. 4 and 5 would be 150 GPH. The overall dimensions of this type of bank is expected to be approximately 40 by 15 by 15 inches with a weight of about 60 pounds.

By arranging the modules into banks, a number of advantages would be obtained such as that a bank could form a convenient Line Replacement Unit (LRU) with only two couplings to the fuel system and with only a small number of external electrical connections. All other mechanical and electrical connections within each module could be made at a factory where the banks are assembled. A single pressurization system connected to each module can be used. Another advantage is that systems of different sizes and flow rates can be configured by assembling varying number of banks. Furthermore, the overall shape or form factor of the system can be varied to suit unique mounting consideration in different applications The prototype's driver electronics unit 6 contained three sections, a function generator, a power amplifier and a power supply. The function generator had a frequency range from 0.01 Hz to 300 kHz and could provide four different wave shapes. Those shapes (sinsoidal, triangular, half-square and full-square) have different spectral compositions and excite the ceramic rings at different efficiencies. The electronics unit allowed the excitation to be tuned to optimal frequencies. The power amplifier section was a commercial unit modified to provide a signal response up to 70 kHz. Its power output was 300 W at 15 kHz tapering to 32 W at 59 kHz. When the piezoelectric elements are driven below 40 kHz, the power transferred is at least 60 W. A high-voltage transformer takes the power amplifier output of 70 V and steps it up to approximately 1000 V in order to provide the voltage required by the piezoelectric elements. The ultrasonic frequencies can range from 22 kHz to 40 kHz or higher. In the prototype apparatus, that frequency was variable along with the power supplied to it in order to optimize the performance.

Various modifications may be made to the preferred embodiments without departing from the spirit and scope of the invention as defined in the appended claims. The module described herein has a flow through pipe but the treatment container could be, for instance, an open tank.

The embodiments of the invention in which an exclusive property or privilege is contained is claimed are defined as follows:

1. An apparatus for the ultrasonic treatment of a microbiology contaminated liquid comprising, a module having a treatment container and an ultrasonic generating means for subjecting ultrasonic vibrations on liquid in the container whereby contaminated liquid in the container subjected to the ultrasonic vibrations result in cavitation in that liquid and the destruction of microorganisms contained therein, the ultrasonic generating means being located outside of the container and submerged in a transmission fluid in an outer container, which fluid contacts an outside surface of the treatment container and the apparatus having a pressurization means for the transmission fluid in order to pressurize the transmission fluid to a controlled level and prevent cavitation occurring at areas surrounding the ultrasonic generating means, the outer container having an interior and said pressurization means comprising a hydraulic cylinder connected to the interior of the outer container for applying a pressure to the transmission fluid in the outer container.

2. An apparatus as defined in claim 1, wherein the treatment container is a pipe through which the liquid can continuously flow and the ultrasonic vibration generating means is at least one piezoelectric ceramic ring surrounding the pipe.

3. An apparatus as defined in claim 2, wherein a number of said ceramic rings are co-axial with the pipe, each ring being located adjacent to another ring.

4. An apparatus as defined in claim 3, wherein the transmission fluid is an oil.

5. An apparatus as defined in claim 4, wherein a number of modules are connected in parallel with inputs to each of said pipes being connected to an input manifold and outputs of each pipe being connected to an output manifold to form a bank of modules.

6. An apparatus as defined in claim 4, wherein the pipe is stainless steel and extends through the outer container that has a fill hole for the oil and an air vent to vent air from the container as it is filled with the oil and means to seal the air vent once the container is filled with oil.

7. An apparatus as defined in claim 6, wherein the ceramic rings are fixed in the outer container by a support attached to the outer container.

8. An apparatus as defined in claim 2 wherein a number of modules are connected in parallel with inputs to each of said pipes being connected to an input manifold and outputs of each pipe being connected to an output manifold to form a bank of modules wherein transmission fluid in the modules is pressurized by a single hydraulic cylinder connected to all of the outer containers, the cylinder being provided with means to apply a predetermined pressure to a piston in the hydraulic cylinder.

9. An apparatus as defined in claim 8, wherein an equal number of modules are provided on each side of a central support structure.

10. An apparatus as defined in claim 6, wherein a circular groove extends around an inner top surface of the outer container, an end of said air vent opening into said groove.

11. An apparatus as defined in claim 1 further comprising an air cylinder for loading said hydraulic cylinder.

12. An apparatus as defined in claim 1 wherein said ultrasonic generating means generates said ultrasonic vibrations in a frequency range of 22 kHz to 40 kHz.

* * * * *